United States Patent
Takahashi et al.

(10) Patent No.: US 10,679,514 B2
(45) Date of Patent: Jun. 9, 2020

(54) TRAINING SYSTEM AND ANKLE-JOINT TORQUE ESTIMATING METHOD

(71) Applicant: TOYOTA JIDOSHA KABUSHIKI KAISHA, Toyota-shi, Aichi-ken (JP)

(72) Inventors: Masahiro Takahashi, Nagakute (JP); Takahiro Fujishima, Anjo (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 198 days.

(21) Appl. No.: 15/826,023

(22) Filed: Nov. 29, 2017

(65) Prior Publication Data
US 2018/0165982 A1    Jun. 14, 2018

(30) Foreign Application Priority Data
Dec. 9, 2016 (JP) ................. 2016-239332

(51) Int. Cl.
*A61H 1/02* (2006.01)
*G09B 9/052* (2006.01)
(Continued)

(52) U.S. Cl.
CPC .............. *G09B 9/052* (2013.01); *A61H 1/02* (2013.01); *A61H 1/0218* (2013.01); *A61H 1/0266* (2013.01); *A63B 23/04* (2013.01); *A63B 23/08* (2013.01); *A63B 24/00* (2013.01); *B62K 11/007* (2016.11); *G09B 19/0038* (2013.01);
(Continued)

(58) Field of Classification Search
None
See application file for complete search history.

(56) References Cited

U.S. PATENT DOCUMENTS

| 2010/0030442 A1 | 2/2010 | Kosaka |
| 2011/0060518 A1 | 3/2011 | Kosaka |

(Continued)

FOREIGN PATENT DOCUMENTS

| CN | 102341298 A | 2/2012 |
| CN | 105425802 A | 3/2016 |

(Continued)

OTHER PUBLICATIONS

Communication issued by the USPTO dated Feb. 7, 2019 in U.S. Appl. No. 15/663,925.

(Continued)

*Primary Examiner* — Bruk A Gebremichael
(74) *Attorney, Agent, or Firm* — Sughrue Mion, PLLC

(57) ABSTRACT

A training system includes: an inverted-pendulum mobile body including a drive wheel and a riding portion on which a rider rides in a standing position; a first detecting unit configured to detect a driving torque that is applied to the drive wheel to maintain the inverted-pendulum mobile body in an inverted state; a second detecting unit configured to detect a load applied by the rider to an assisting support portion configured to assist the rider in maintaining a balance; and an output unit configured to generate torque information about an ankle-joint torque applied by the rider to the riding portion, based on the driving torque detected by the first detecting unit and the load detected by the second detecting unit, and configured to output the torque information.

10 Claims, 11 Drawing Sheets

(51) Int. Cl.
*A63B 23/04* (2006.01)
*A63B 24/00* (2006.01)
*A63B 23/08* (2006.01)
*G09B 19/00* (2006.01)
*B62K 11/00* (2006.01)
*A61B 5/107* (2006.01)
*A61B 5/00* (2006.01)
*A61B 5/103* (2006.01)

(52) U.S. Cl.
CPC ........... *A61B 5/1036* (2013.01); *A61B 5/1071* (2013.01); *A61B 5/4528* (2013.01); *A61B 5/4595* (2013.01); *A61B 5/6895* (2013.01); *A61B 2503/10* (2013.01); *A61H 2201/0173* (2013.01); *A61H 2201/1215* (2013.01); *A61H 2201/1261* (2013.01); *A61H 2201/163* (2013.01); *A61H 2201/164* (2013.01); *A61H 2201/1652* (2013.01); *A61H 2201/1671* (2013.01); *A61H 2201/50* (2013.01); *A61H 2201/5025* (2013.01); *A61H 2201/5035* (2013.01); *A61H 2201/5043* (2013.01); *A61H 2201/5046* (2013.01); *A61H 2201/5058* (2013.01); *A61H 2201/5061* (2013.01); *A61H 2201/5084* (2013.01); *A61H 2203/0406* (2013.01)

(56) References Cited

U.S. PATENT DOCUMENTS

| | | |
|---|---|---|
| 2011/0282532 A1 | 11/2011 | Kosaka et al. |
| 2012/0158208 A1* | 6/2012 | Kawamoto .......... B62K 11/007 701/1 |
| 2012/0166048 A1 | 7/2012 | Inoue et al. |
| 2013/0171601 A1 | 7/2013 | Yuasa et al. |
| 2015/0066276 A1* | 3/2015 | Nakashima .......... B62K 11/007 701/22 |
| 2015/0239499 A1 | 8/2015 | Lan et al. |
| 2015/0298756 A1* | 10/2015 | Takeda .................. B62K 23/08 180/218 |
| 2017/0106931 A1 | 4/2017 | Wood |
| 2018/0057099 A1 | 3/2018 | Otsuki et al. |

FOREIGN PATENT DOCUMENTS

| | | |
|---|---|---|
| JP | 2004-180982 A | 7/2004 |
| JP | 2006-74270 A | 3/2006 |
| JP | 2006-256401 A | 9/2006 |
| JP | 2010-030436 A | 2/2010 |
| JP | 2011-031669 A | 2/2011 |
| JP | 2011-140262 A | 7/2011 |
| JP | 2012-70802 A | 4/2012 |
| JP | 2012-86683 A | 5/2012 |
| JP | 2014-182318 A | 9/2014 |
| JP | 2016-49950 A | 4/2016 |
| JP | 2016-74271 A | 5/2016 |
| JP | 2016-141326 A | 8/2016 |

OTHER PUBLICATIONS

Notice of Allowance dated May 1, 2019 issued by the United States Patent and Trademark Office in U.S. Appl. No. 15/663,925.

* cited by examiner

TRAINING SYSTEM AND ANKLE-JOINT TORQUE ESTIMATING METHOD

INCORPORATION BY REFERENCE

The disclosure of Japanese Patent Application No. 2016-239332 filed on Dec. 9, 2016 including the specification, drawings and abstract is incorporated herein by reference in its entirety.

BACKGROUND

1. Technical Field

The disclosure relates to a training system and an ankle-joint torque estimating method.

2. Description of Related Art

There are traveling apparatuses configured to detect attitude information with the use of, for example, a gyro sensor and an acceleration sensor, and to execute drive control based on the detected attitude information. Examples of such traveling apparatuses include an inverted-pendulum two-wheeled vehicle configured to control drive wheels thereof through the application of an attitude control model of an inverted pendulum. For example, Japanese Patent Application Publication No. 2010-30436 describes an inverted-pendulum two-wheeled vehicle that travels forward or makes a turn in response to a rider's tilting operation of a handle.

SUMMARY

An inverted-pendulum two-wheeled vehicle may be used as a training apparatus like a bicycle, rather than a tool just for traveling. When an inverted-pendulum two-wheeled vehicle is used as a training apparatus, it is preferable to make an objective observation of how much training load the rider receives. However, in order to make an observation of a training load, a measuring device needs to be fitted to a rider's body. In terms of convenience, there is still room for improvement.

The disclosure makes it possible to quantitatively observe an ankle-joint torque of a rider riding on an inverted-pendulum mobile body, without the need to fit a special device, such as a sensor, to the rider's body.

A training system according to a first aspect of the disclosure includes: an inverted-pendulum mobile body including a drive wheel and a riding portion on which a rider rides in a standing position; a first detecting unit configured to detect a driving torque that is applied to the drive wheel to maintain the inverted-pendulum mobile body in an inverted state; a second detecting unit configured to detect a load applied by the rider to an assisting support portion configured to assist the rider in maintaining a balance; and an output unit configured to generate torque information about an ankle-joint torque applied by the rider to the riding portion, based on the driving torque detected by the first detecting unit and the load detected by the second detecting unit, and configured to output the torque information.

With this configuration, the rider or an assistant who assists the rider can objectively acquire a training load on an ankle of the rider without fitting a special device, such as a sensor, to the rider. In particular, the torque information about the ankle-joint torque is generated in consideration of the load applied by the rider to the assisting support portion, such as a handle. Thus, the training load on the rider can be evaluated with a higher degree of accuracy.

The training system according to the above aspect may include a notifying unit configured such that, when the load detected by the second detecting unit has exceeded a threshold load set in advance, the notifying unit notifies the rider of a fact that the load has exceeded the threshold load. Provision of the notifying unit allows the rider to correct the riding attitude during the training. The notifying unit may notify the rider of the fact that the load has exceeded the threshold load, by sound, light, or vibrations. The output unit may be configured to output the torque information after adding additional information to the torque information when the load detected by the second detecting unit has exceeded the predetermined threshold load. By adding the additional information in this way, it is possible to acquire the situations of the rider more accurately when the training statuses of the rider are checked after the training.

The assisting support portion may include a handle provided in the inverted-pendulum mobile body and configured to be held by the rider. The assisting support portion may include a hanging tool provided independently of the inverted-pendulum mobile body and fitted to an upper body of the rider. Even with assisting support portions having various configurations for supporting the rider, it is possible to generate accurate torque information about each of the assisting support portions.

The training system according to the above aspect may include an acquiring unit configured to acquire at least one of a body weight of the rider and a foot size of the rider. The output unit may be configured to generate the torque information based on the driving torque, the load, and the at least one of the body weight and the foot size acquired by the acquiring unit. By acquiring such information, the torque information can be generated with a higher degree of accuracy. Alternatively, the output unit may be configured to generate the torque information based on the driving torque, the load, and at least one of a body weight of the rider and a foot size of the rider that are set in advance as fixed values. When at least one of the parameters is set as a fixed value, it is no longer necessary for the rider to input the accurate value of the parameter.

The training system according the above aspect may include a switching unit configured to execute switching between an active mode and a passive mode each set as a training mode in which an ankle joint of the rider is trained. The active mode is a mode in which the inverted-pendulum mobile body travels in response to shifting of the rider's center of gravity, and the passive mode is a mode in which a simulative disturbance is generated to make the inverted state unstable. When the training system has a plurality of modes as described above, it is possible to provide training programs in accordance with the situations of the rider. The training system according to the above aspect may include a tilt control unit configured to tilt the riding portion based on the torque information output from the output unit. When the tilt control is executed, it is possible to provide a more effective training program to the rider.

The output unit may be configured to generate the torque information based on the driving torque at a time when the inverted-pendulum mobile body is not making a turn. By setting a condition for outputting the torque information as described above, the reliability of the generated torque information can be improved.

The training system according to the above aspect may include a presenting unit configured to count the number of times the ankle-joint torque is estimated to exceed a threshold value set in advance, based on the torque information output from the output unit, and configured to present the number of times the ankle-joint torque is estimated to exceed the threshold value. Provision of the presenting unit allows the rider to easily acquire a training progress status of the rider.

An ankle-joint torque estimating method according to a second aspect of the disclosure includes: detecting a driving torque that is applied to a drive wheel of an inverted-pendulum mobile body to maintain the inverted-pendulum mobile body in an inverted state, the inverted-pendulum mobile body including the drive wheel and a riding portion on which a rider rides in a standing position; detecting a load applied by the rider to an assisting support portion configured to assist the rider in maintaining a balance; and generating an estimated value of an ankle-joint torque of the rider based on the driving torque and the load.

By generating the estimated value of the ankle-joint torque according to the method, it is possible to provide information for objectively acquiring a training load on an ankle of the rider, without fitting a special device, such as a sensor, to the rider. In particular, the torque information about the ankle-joint torque is generated in consideration of a load applied by the rider to an assisting support portion, such as a handle. Thus, the torque information is accurate as information about the training load.

The disclosure makes it possible to quantitatively observe an ankle-joint torque of a rider riding on an inverted-pendulum mobile body, without time and effort to fit a special device, such as a sensor, to the rider in advance.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Hereinafter, the disclosure will be described based on the following embodiments. However, the following embodiments are not intended to limit the disclosure. Moreover, it is not absolutely necessary to provide all the configurations to be described in the following embodiments.

Figure 1:
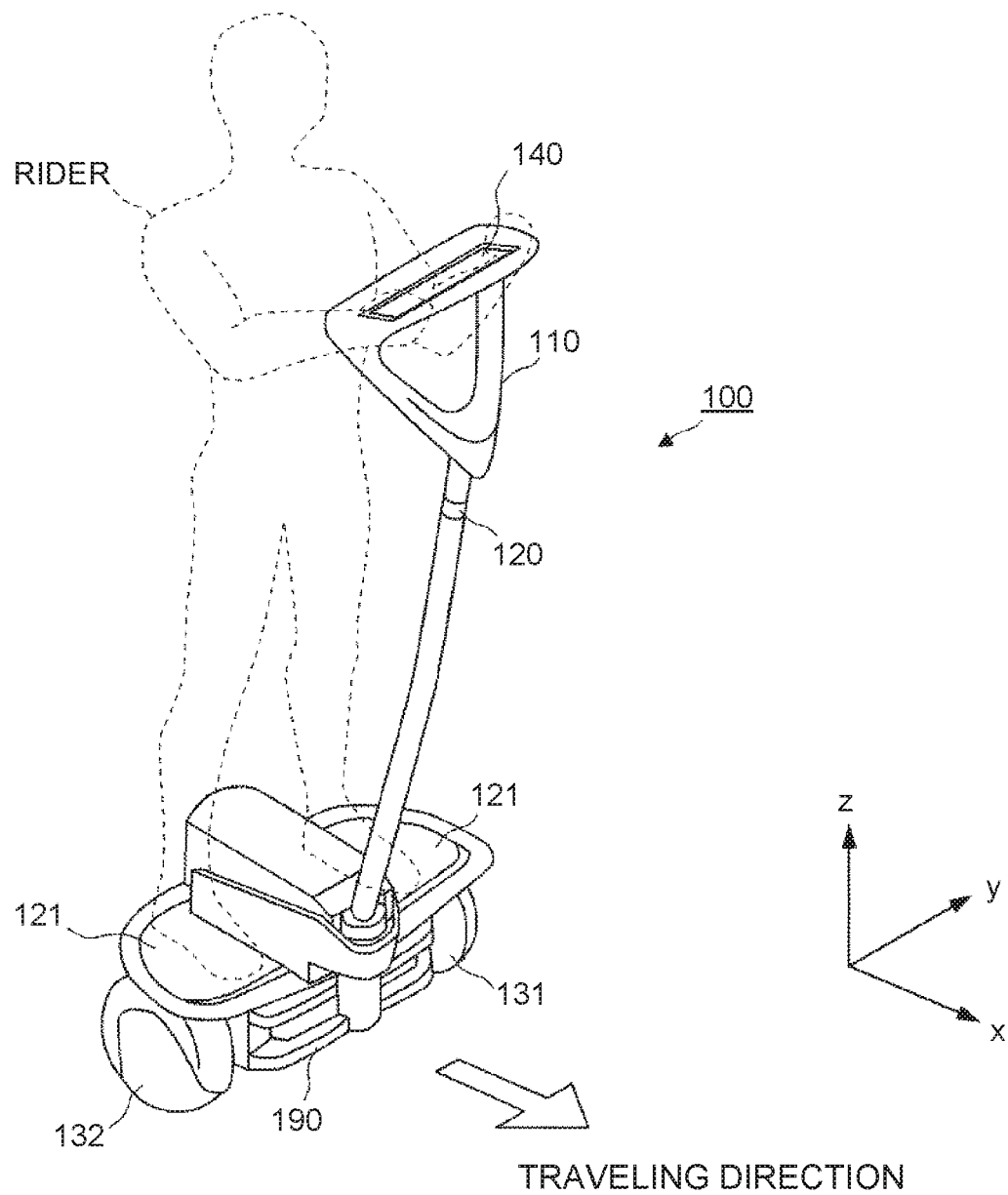
FIG. 1 is a perspective view of the appearance of an inverted two-wheeled vehicle according to an embodiment.

FIG. 1 is a perspective view of the appearance of an inverted two-wheeled vehicle 100 serving as a training system according to a present embodiment. The present embodiment will be described on the assumption that the inverted two-wheeled vehicle 100 is an inverted-pendulum mobile body and the inverted two-wheeled vehicle 100 constitutes the entirety of the training system.

The inverted two-wheeled vehicle 100 includes a base 190, a handle 110, a riding base 121, and right and left wheels 132, 131. The base 190 constitutes the whole framework of the inverted two-wheeled vehicle 100, and is equipped with the handle 110, the riding base 121, and the right and left wheels 132, 131. A rider's right foot is placed on the right portion of the riding base 121, and the rider's left foot is placed on the left portion of the riding base 121. The handle 110 includes a support rod coupled to the base 190, and a held portion to be held by the rider. When the handle 110 is held by the rider, the handle 110 functions as an assisting support portion that assists the rider in maintaining the balance.

The support rod of the handle 110 is provided with a load sensor 120 that is, for example, a load cell to which strain gauges are bonded. The load sensor 120 is configured to detect a load with which the rider pushes or pulls the handle 110. The held portion of the handle 110 is provided with a display unit 140 such that the rider can see the display unit 140. The display unit 140 is, for example, a liquid crystal panel and configured to provide various kinds of information to the rider.

The inverted two-wheeled vehicle 100 according to the present embodiment is configured on the assumption that a rider rides thereon in a standing position. The riding base 121 functions as a riding portion on which the rider's right foot and left foot are placed. The riding base 121 may be fixed to the base 190 or may be provided with a linkage mechanism such that a riding surface is tilted in the right-left direction as the inverted two-wheeled vehicle 100 makes a right turn or makes a left turn.

The left wheel 131 is attached to the riding base 121 so as be offset leftward from the center of the riding base 121, and is a drive wheel that is rotationally driven by a motor (described later). The right wheel 132 is attached to the riding base 121 so as be offset rightward from the center of the riding base 121, and is a drive wheel that is rotationally driven by a motor (described later). The left wheel 131 and the right wheel 132 are disposed in parallel to each other and coaxially with each other. With this configuration, when the left wheel 131 and the right wheel 132 are rotated in the same direction and at the same speed, the inverted two-wheeled vehicle 100 travels straight, whereas when the left wheel 131 and the right wheel 132 are rotated at different speeds, the inverted two-wheeled vehicle 100 makes a right turn or a left turn.

The inverted two-wheeled vehicle 100 according to the present embodiment is a coaxial two-wheeled vehicle configured to control rotations of the wheels 131, 132, which are drive wheels, based on an attitude control model of an inverted pendulum. A controller (described later) is configured to detect an attitude of the entirety of the inverted two-wheeled vehicle 100 on which a rider is riding and to control rotational driving of the wheels 131, 132 such that a state where the rider is riding on the inverted two-wheeled vehicle 100 is stably maintained. This control allows the rider to move the inverted two-wheeled vehicle 100 in a direction in which the rider intends to travel, by shifting the rider's center of gravity in this direction. By shifting the rider's center of gravity forward, the rider moves the inverted two-wheeled vehicle 100 forward. By shifting the rider's center of gravity backward, the rider moves the inverted two-wheeled vehicle 100 backward. By shifting the rider's center of gravity rightward, the rider turns the inverted two-wheeled vehicle 100 to the right. By shifting the rider's center of gravity leftward, the rider turns the inverted two-wheeled vehicle 100 to the left.

The inverted two-wheeled vehicle 100 according to the present embodiment is an apparatus that may serve as rehabilitation equipment for restoring an ankle joint function of a patient having a problem in his/her ankle joint. When a patient as a rider tries to keep riding on the inverted two-wheeled vehicle 100 while maintaining the balance, the inverted two-wheeled vehicle 100 can apply a load in a magnitude that is expected to produce rehabilitation effect, to an ankle joint of the patient. The load corresponds to an ankle-joint torque generated in the ankle joint by the patient. When the ankle-joint torque has a magnitude commensurate with the patient, the rehabilitation effect can be expected. The inverted two-wheeled vehicle 100 according to the present embodiment has a function of quantitatively presenting the ankle-joint torque generated by the rider.

The inverted two-wheeled vehicle 100 can be used not only as rehabilitation equipment but also as a traveling apparatus for traveling to a destination. When the inverted two-wheeled vehicle 100 is used as a traveling apparatus, not only a patient having a problem in his/her ankle joint but also a healthy person can use the inverted two-wheeled vehicle 100. The inverted two-wheeled vehicle 100 has a normal mode in which the inverted two-wheeled vehicle 100 is used as a traveling apparatus, and a training mode in which the inverted two-wheeled vehicle 100 is used as rehabilitation equipment. When the normal mode is selected, the inverted two-wheeled vehicle 100 is allowed to make a right turn and a left turn. On the other hand, when the training mode is selected, the inverted two-wheeled vehicle 100 is prohibited from making a right turn and a left turn. The following description will be provided on the assumption that a patient having a problem in his/her ankle joint is a rider of the inverted two-wheeled vehicle 100.

The coordinate system of the inverted two-wheeled vehicle 100 is defined such that a forward traveling direction perpendicular to an axle direction that connects the wheels 131, 132 to each other is an x-axis positive direction, a direction along the axle direction that connects the wheels 131, 132 to each other and toward the wheel 131 is a y-axis positive direction, and a direction perpendicular to both the x-axis and the y-axis and toward the rider's head is a z-axis positive direction, as illustrated in the drawings. Hereinafter, the coordinate system defined in this manner will be used to indicate directions in the drawings.

Figure 2:
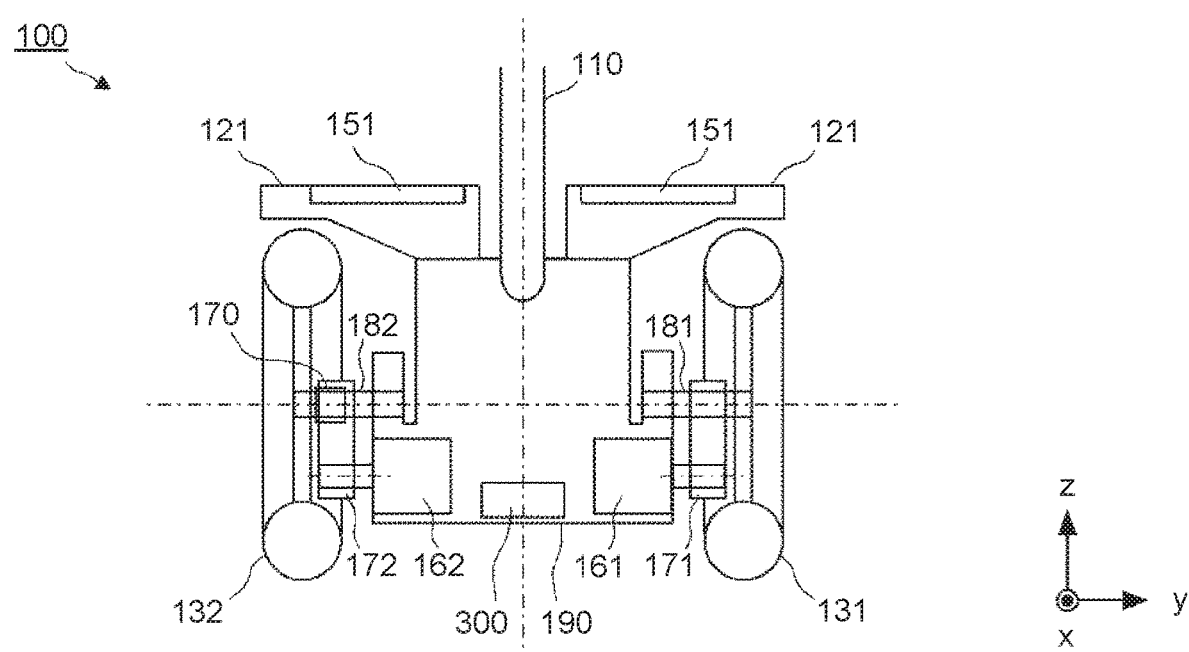
FIG. 2 is a schematic diagram illustrating the main configuration of the inverted two-wheeled vehicle.

FIG. 2 is a schematic diagram illustrating the main configuration of the inverted two-wheeled vehicle 100. Specifically, FIG. 2 schematically illustrates a section of the inverted two-wheeled vehicle 100 taken along a yz plane, as viewed from the positive side in the x-axis direction.

The two wheels, that is, the right and left wheels 132, 131 are rotatably supported by the base 190 such that axles 182, 181 of the wheels 132, 131 are aligned in a straight line. A motor 161 configured to drive the left wheel 131 and a motor 162 configured to drive the right wheel 132 are fixedly provided in the base 190. A driving force generated by the motor 161 is transmitted to the axle 181 via a transmission mechanism 171 that serves also as a speed reducer, thereby rotating the wheel 131. A driving force generated by the motor 162 is transmitted to the axle 182 via a transmission mechanism 172 that serves also as a speed reducer, thereby rotating the wheel 132. That is, the wheels 131, 132 are controlled to be rotationally driven respectively by the motors 161, 162 that are independent of each other and the transmission mechanisms 171, 172 that are independent of each other.

The axle 182 is provided with a torque sensor 170. The torque sensor 170 is configured to detect a motor torque that is output from the motor 162 to the wheel 132. The torque sensor 170 is, for example, a sensor configured such that strain gauges are bonded to a shaft to detect torsional deformation of the shaft. The torque sensor 170 is provided on the axle 182 and is not provided on the axle 181 in the inverted two-wheeled vehicle 100 according to the present embodiment. However, a torque sensor 170 may be provided also on the axle 181 in order to achieve a higher degree of accuracy. When the torque sensors 170 are respectively provided on the axles 181, 182, outputs from the two torque sensors 170 may be averaged to calculate a motor torque (described later). Depending on the degree of accuracy of a motor torque to be detected, current values of electricity supplied to the motors 161, 162 may be detected and the current values may be converted into a motor torque, instead of providing the torque sensor 170.

Load sensors 151 are load sensors that are embedded in the riding base 121 and configured to detect the fact that the rider has placed his/her feet on the riding base 121. Each load sensor 151 is, for example, a mechanical switch that is closed when being pressurized.

A battery 300 is a secondary battery, such as a lithium-ion battery, and supplies electricity to the motors 161, 162 and so forth via, for example, a transformer circuit. The secondary battery may be configured to be rechargeable from, for example, a household alternating-current (AC) power source and configured to be detachable.

Figure 3:
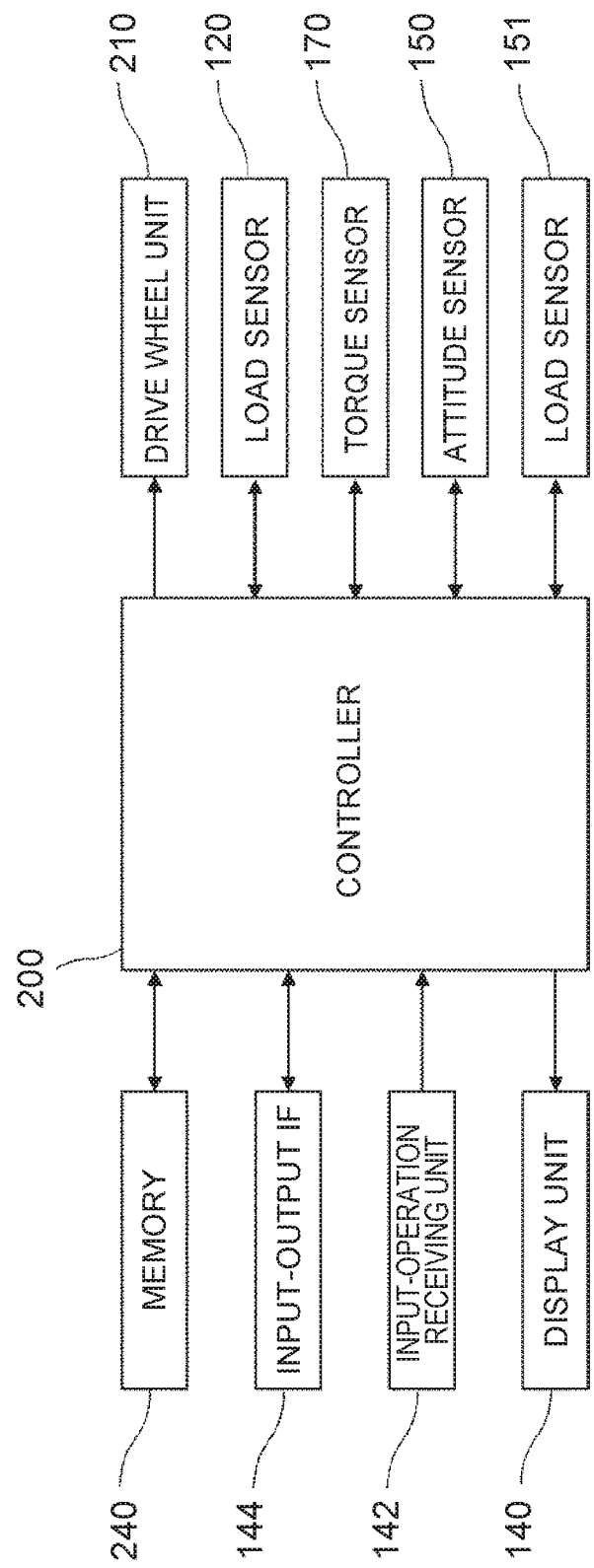
FIG. 3 is a control block diagram of the inverted two-wheeled vehicle.

FIG. 3 is a control block diagram of the inverted two-wheeled vehicle 100. A controller 200 is, for example, a central processing unit (CPU) and provided in the base 190. The controller 200 is configured to collectively control the elements of the inverted two-wheeled vehicle 100. A drive wheel unit 210 includes driving circuits and the motors 161, 162 for driving the wheels 131, 132. The controller 200 transmits drive signals to the drive wheel unit 210, thereby controlling the rotations of the wheels 131, 132.

The load sensor 120 transmits a detection signal to the controller 200 in response to a request signal from the controller 200. The detection signal includes, for example, output signals from a plurality of strain gauges that are bonded, in different orientations, to the support rod of the handle 110. Based on the detection signal, the controller 200 can acquire the direction and magnitude of a load applied to the handle 110 by the rider. That is, the load sensor 120 functions as a detecting unit configured to detect a load applied to the handle 110 by the rider, in cooperation with the controller 200.

The torque sensor 170 transmits a detection signal to the controller 200 in response to a request signal from the controller 200. Based on the detection signal, the controller 200 calculates a motor torque that is output from the motor 162 to the wheel 132 in order to maintain the inverted two-wheeled vehicle 100 in an inverted state. That is, the torque sensor 170 functions as a detecting unit configured to detect a driving torque that is applied to the drive wheel in order to maintain the inverted two-wheeled vehicle 100 in the inverted state, in cooperation with the controller 200.

An attitude sensor 150 includes an acceleration sensor and a gyro sensor, and is configured to transmit detection signals to the controller 200 in response to a request signal from the controller 200. Based on these detection signals, the controller 200 recognizes the inverted state of the inverted two-wheeled vehicle 100, generates a drive signal required to maintain the inverted state, and transmits the drive signal to the drive wheel unit 210.

Each load sensor 151 is configured to transmit a detection signal to the controller 200 in response to a request signal from the controller 200. Upon reception of the detection signals, the controller 200 recognizes that the rider has ridden on the inverted two-wheeled vehicle 100, and starts attitude control of the inverted pendulum.

The display unit 140 is configured to display various kinds of information to be provided to the rider, in accordance with a display signal from the controller 200. When the training mode in which the rider undergoes rehabilitation has been selected, the display unit 140 displays torque information about an ankle-joint torque of the rider, which is calculated by the controller 200, in addition to training menu items and a training progress status. That is, the display unit 140 functions as an output unit configured to output the torque information detected by the detecting unit, in cooperation with the controller 200.

An input-operation receiving unit 142 includes, for example, a touch panel that is provided to be superimposed on the liquid crystal panel of the display unit 140, and operation members, such as switches, provided on the handle 110 to be operated by the rider. The input-operation receiving unit 142 receives an input operation performed by the rider, and transmits an input signal to the controller 200. The rider provides, for example, the selection of a mode and initial input parameters (described later) to the controller 200 via the input-operation receiving unit 142. That is, the input-operation receiving unit 142 functions as an acquiring unit configured to acquire information and instructions from the rider, in cooperation with the controller 200. Upon reception of the selection of an active mode (described later) or a passive mode (described later) from the rider via the input-operation receiving unit 142, the controller 200 switches the mode to a mode selected by the rider. In this case, the input-operation receiving unit 142 functions as a switching unit configured to switch the mode between the active mode and the passive mode, in cooperation with the controller 200.

An input-output interface (IF) 144 includes an input interface configured to receive information from an external device, and an output interface configured to output information to an external device. The input-output IF 144 is, for example, a wireless local area network (LAN) interface or a universal serial bus (USB) interface. When outputting torque information to an external device, the controller 200 outputs the torque information via the input-output IF 144. In this case, the input-output IF 144 functions as an output unit configured to output the torque information, in cooperation with the controller 200. In addition, the controller 200 can receive, for example, initial input parameters from an external device via the input-output IF 144. In this case, the input-output IF 144 functions as an acquiring unit configured to acquire information about the rider, in cooperation with the controller 200.

A series of control programs is stored in a memory 240 in advance. At the time of startup, the controller 200 reads the control programs from the memory 240 and executes various controls. The memory 240 is a nonvolatile storage medium, such as a solid state drive. The memory 240 stores, in addition to the control programs, various parameter values, functions, look-up tables, and so forth that are used in the controls.

Figure 4:
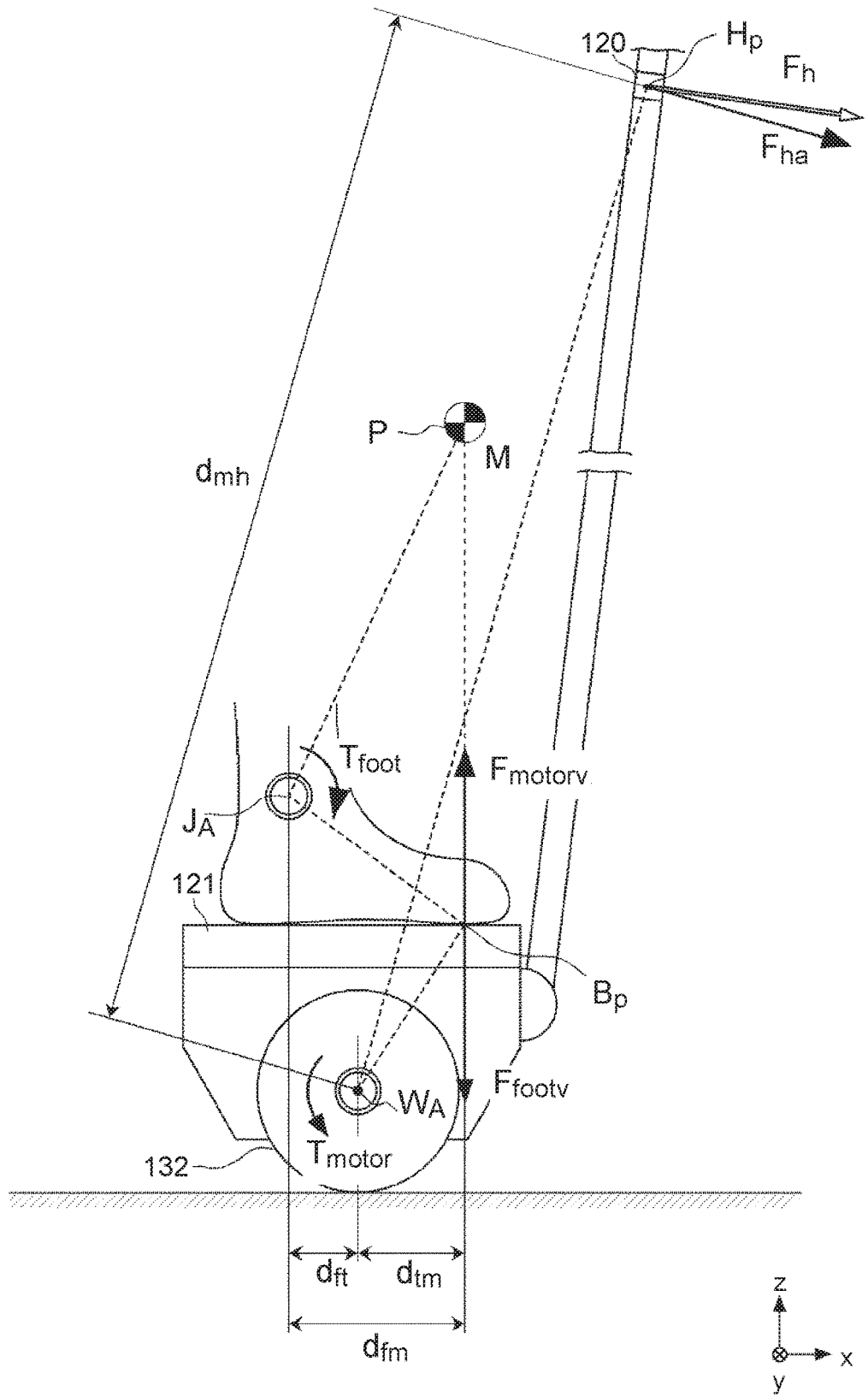
FIG. 4 is a diagram illustrating the principle of detection of an ankle-joint torque.

Next, description will be provided on the principle of how to detect an ankle-joint torque of the rider based on the detected motor torque. FIG. 4 is a diagram illustrating the principle of detection of an ankle-joint torque. FIG. 4 schematically illustrates a situation where the wheel 132 to which the torque sensor 170 is coupled and the riding base 121 on which the rider's right foot has been placed are viewed from the right side with respect to the traveling direction.

As illustrated in FIG. 4, $W_A$ denotes a rotation center position of the wheel 132, $J_A$ denotes an ankle-joint center position of the right foot, P denotes a position of the center of gravity of the combination of the rider and the inverted two-wheeled vehicle 100, and $B_P$ denotes a foot of a perpendicular extending from P to the riding surface. In addition, M denotes a mass of the combination of the rider and the inverted two-wheeled vehicle 100, $T_{foot}$ denotes an ankle-joint torque, and $T_{motor}$ denotes a motor torque. Moreover, $d_{fm}$ denotes a distance from $J_A$ to $B_P$ in the x-axis direction, $d_{ft}$ denotes a distance from $J_A$ to $W_A$ in the x-axis direction, and $d_{tm}$ denotes a distance from $W_A$ to $B_P$ in the x-axis direction.

In addition, $H_P$ denotes a position of the load sensor 120, and $F_h$ denotes a force detected by the load sensor 120. Further, $F_{ha}$ denotes a component that is included in $F_h$ and that is perpendicular to a line connecting $W_A$ to $H_P$. Furthermore, $d_{mh}$ denotes a distance between $W_A$ and $H_P$.

First, a state where the rider has not applied any force to the handle 110, that is, a state where $F_h$ is zero will be described. At this time, $F_{motorv}$ that is a force in a vertical direction generated by the motor is balanced, at $B_P$, with $F_{footv}$ that is a force in the vertical direction generated by the ankle joint, and Expression (1) is satisfied.

$$F_{motorv}=F_{footv} \quad \text{Expression (1)}$$

When Expression (1) is converted into a relational expression of torque, Expression (2) is satisfied.

$$T_{foot}/d_{fm}=T_{motor}/d_{tm} \quad \text{Expression (2)}$$

Therefore, $T_{foot}$, which is a response variable, is expressed by Expression (3).

$$T_{foot}=T_{motor}*d_{fm}/d_{tm} \quad \text{Expression (3)}$$

Furthermore, the relationship between the distances in the x-axis direction is expressed by Expression (4).

$$d_{fm}=d_{ft}+d_{tm} \quad \text{Expression (4)}$$

When the relationship expressed by Expression (4) is substituted into Expression (3), Expression (5) is satisfied.

$$T_{foot}=T_{motor}*(d_{ft}/d_{tm}+1) \quad \text{Expression (5)}$$

Since $d_{tm}$ denotes the distance from $W_A$ to $B_P$ in the x-axis direction, $d_{tm}$ is expressed by Expression (6).

$$d_{tm}=T_{motor}/(Mg) \quad \text{Expression (6)}$$

Here, g denotes a gravitational acceleration. Then, Expression (5) can be solved as expressed by Expression (7).

$$T_{foot}=Mg*d_{ft}+T_{motor} \quad \text{Expression (7)}$$

The first term $Mg*d_{ft}$ on the right side of Expression (7) includes specific information about the rider. Specifically, the first term includes the mass of the rider and the ankle joint center position $J_A$. To be brief, assumed values of the mass of the rider and the ankle joint center position $J_A$ can be set based on a standard human body model. For example, assuming that the rider has a body weight of 60 kg, M can be calculated because the mass of the inverted two-wheeled vehicle 100 is known. Further, assume that a standard value of foot length is 26 cm. Statistics show that the ankle joint center position $J_A$ is apart from a heel end by 22% of the foot length, and a neutral position of a human body is apart from the heel end by 45% of the foot length. In a stationary state, the rider rides on the riding base 121 such that the neutral position of the human body is located over the axles. In consideration of this, $d_{fi}$ can be set as $d_{fi}=26\times(0.45-0.22)= 5.98$ cm. When such an assumed value is used, the first term can be simply calculated.

When at least one of the body weight and the foot size of the rider is acquired as an initial input parameter via the input-operation receiving unit 142 or the input-output IF 144, it is possible to calculate the first term with a higher degree of accuracy. The initial input parameter need not be input by the rider. If, for example, the load sensor 151 can measure the body weight or the foot size of the rider, these values can be automatically acquired when the rider rides on the riding base 121.

Next, a state where the rider has applied a force to the handle 110, that is, a state where $F_h$ is not zero will be described. The support rod of the handle 110 is fixed to the base 190, and the position $H_P$ of the load sensor 120 is unchanged relative to the rotation center position $W_A$ of the wheel 132. Therefore, the direction of $F_{ha}$ remains constant. Consequently, based on a detection signal from the load sensor 120, the controller 200 can calculate an angle $\theta$ formed between the $F_h$ and $F_{ha}$, and can calculate $F_{ha}$ according to Expression (8).

$$F_{ha}=F_h*\cos\theta \qquad \text{Expression (8)}$$

When $T_h$ denotes a torque around $W_A$ due to $F_{ha}$ that is generated as the rider applies a force to the handle 110, $T_h$ can be expressed by Expression (9).

$$T_h=F_{ha}*d_{mh} \qquad \text{Expression (9)}$$

Consequently, when the rider applies a force to the handle 110, Expression (7) can be corrected into Expression (10).

$$T_{foot}=Mg*d_{fi}+T_{motor}-T_h \qquad \text{Expression (10)}$$

Note that, in the foregoing expression, a component $F_{hb}$ in the gravity direction, which is included in $F_h$, is not taken into consideration because $F_{hb}$ is considerably small and substantially ignorable in the present embodiment. However, when the component $F_{hb}$ is taken into consideration, Mg in Expression (10) is substituted with Mg−$F_{hb}$.

Here, the first term $Mg*d_{fi}$ on the right side of Expression (10) can be regarded as a fixed value that is determined when the rider rides on the riding base 121. On the other hand, the second term and the third term $T_{motor}-T_h$ on the right side of Expression (10) are values that vary from moment to moment while the inverted two-wheeled vehicle 100 undergoes inverted pendulum control. The value of $T_{motor}-T_h$ can be tracked by monitoring an output from the torque sensor 170 and an output from the load sensor 120. That is, it can be said that a variation component of the ankle-joint torque $T_{foot}$ is $T_{motor}-T_h$. Consequently, a time-dependent variation in the ankle-joint torque $T_{foot}$ that is calculated by and output from the controller 200 is correlated with a time-dependent variation in $T_{motor}-T_h$.

It is considered based on such a relationship that, when the time-dependent variation is desired to be output as torque information about the ankle-joint torque, only $T_{motor}-T_h$ may be output. When an actual value of the ankle-joint torque is desired to be output simply, the actual value may be output as the sum of the assumed values and $T_{motor}-T_h$. When an actual value of the ankle-joint torque is desired to be output with a higher degree of accuracy, a value obtained in consideration of specific information about the rider is output as the actual value. In each case, the controller 200 calculates $T_{motor}-T_b$ based on the outputs from the torque sensor 170 and the load sensor 120 to generate the torque information about the ankle joint. In other words, it can be said that the controller 200 estimates an ankle-joint torque based on a motor torque and a load applied to the handle 110.

With the apparatus configured to estimate an ankle-joint torque based on the foregoing principle, it is possible to objectively acquire a training load on an ankle of a patient who carries out training, without the inconvenience of fitting, to the patient, a special device, such as a sensor for measuring a muscle strength, unlike in related art. Moreover, it is possible to quantitatively observe an ankle-joint torque of the patient who is riding on the apparatus in substantially real-time. Therefore, it is possible to carry out training while dynamically adjusting a training time period and a target load amount in accordance with an achievement status of the patient. Even when the rider leans on the handle 110 in order to maintain the balance, an ankle-joint torque at this time can be calculated accurately. Therefore, it is possible to more reliably carry out training for obtaining an effect of rehabilitation.

In Expressions (1) to (10) described above, acceleration in the horizontal direction (the x-axis direction) is not taken into consideration. That is, it can be said that Expression (10) lacks accuracy in a situation where the inverted two-wheeled vehicle 100 travels in the horizontal direction with acceleration. In actual control, however, traveling control with rapid acceleration is hardly executed from the viewpoint of safety of the rider. Therefore, the influence of an acceleration component in the horizontal direction on Expression (10) is relatively small. Therefore, the torque information generated based on Expression (10) suffices from practical viewpoint. When torque estimation is desired to be executed with a higher degree of accuracy, the calculation may be executed based on an output from the torque sensor 170 at the time when no acceleration in the horizontal direction is generated in the inverted two-wheeled vehicle 100.

Similarly, when the influence of an angular acceleration around the z-axis at the time of turning is desired to be eliminated, the calculation may be executed based on an output from the torque sensor 170 at the time when the inverted two-wheeled vehicle 100 is not making a turn. It should be noted that, in the training mode (described later), turning is prohibited, and the influence of angular acceleration around the z-axis is not included in the torque information that is output in the training mode.

Figure 5:
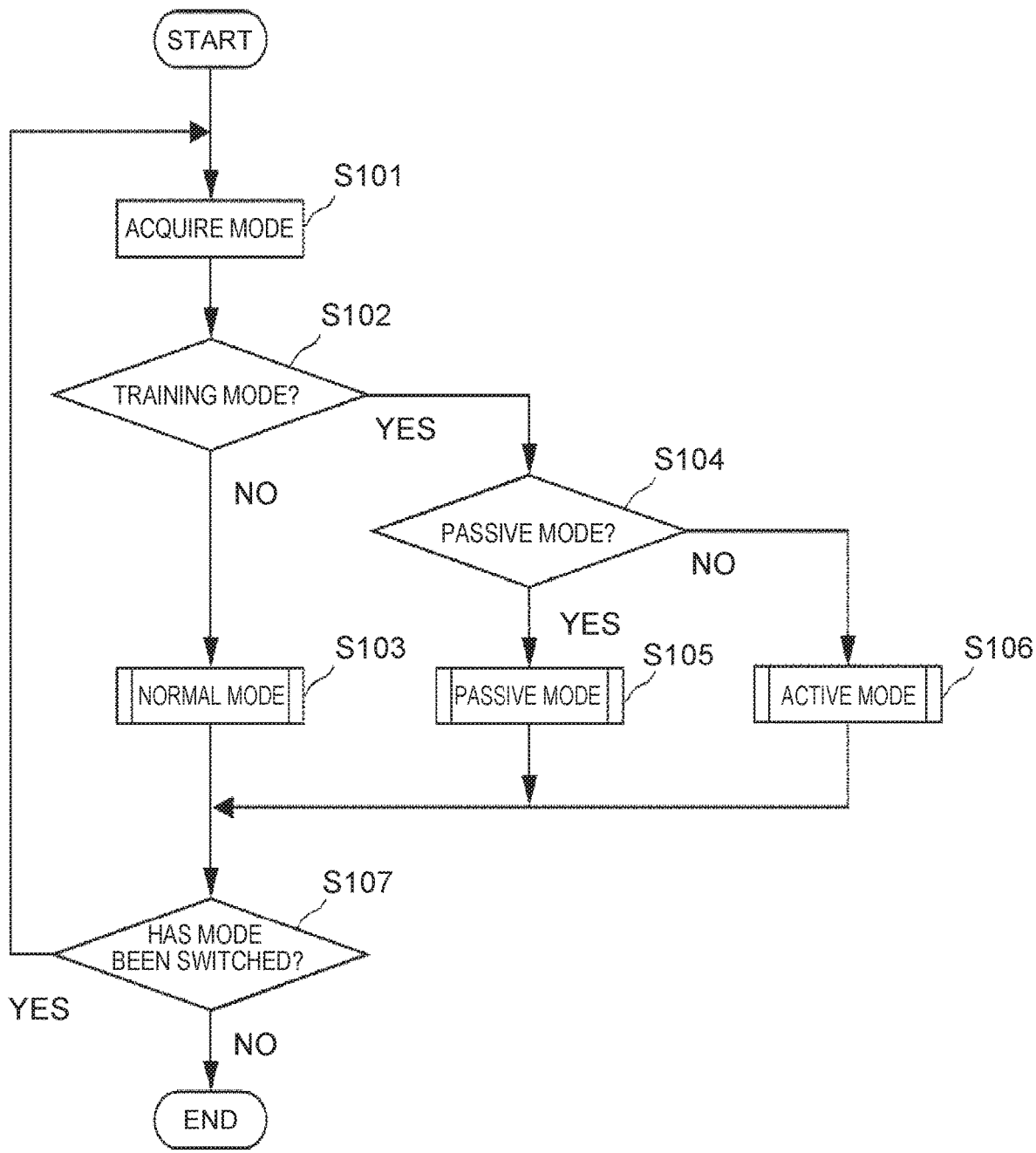
FIG. 5 is a flowchart illustrating an overall control flow of the inverted two-wheeled vehicle.

Next, overall control of the inverted two-wheeled vehicle 100 will be described. FIG. 5 is a flowchart illustrating an overall control flow of the inverted two-wheeled vehicle 100. The inverted two-wheeled vehicle 100 executes a control program that is read from the memory 240 in accordance with a mode selected by a rider.

When a power source for the inverted two-wheeled vehicle 100 is turned on and a series of processes is started, the controller 200 acquires, in step S101, a mode designated by the rider via the input-operation receiving unit 142. In step S102, the controller 200 determines whether the acquired mode is a training mode for carrying out rehabilitation. When the controller 200 determines that the acquired mode is not the training mode, the controller 200 proceeds to step S103 to start control in the normal mode in which the inverted two-wheeled vehicle 100 is used as a traveling apparatus. In the normal mode, the controller 200 causes the inverted two-wheeled vehicle 100 to travel forward, travel backward or make a turn, in response to shifting of the weight of the rider's body. At this time, the torque information about an ankle-joint torque may be displayed on the display unit 140.

When the controller 200 determines in step S102 that the acquired mode is the training mode, the controller 200 proceeds to step S104 to determine whether the acquired mode is the passive mode included in the training mode. When the controller 200 determines that the acquired mode is the passive mode, the controller 200 proceeds to step S105 to execute a training program for the passive mode. When the controller 200 determines that the acquired mode is not the passive mode, the controller 200 proceeds to step S106 to execute a training program for the active mode.

At the completion of a control program in the selected mode, the controller 200 proceeds to step S107 to determine whether the mode is switched by the rider within a predetermined time period. When the controller 200 determines that the mode is switched, the controller 200 repeats the processes from step S101. When the controller 200 determines that the mode is not switched within the predetermined time period, the controller 200 ends the series of processes.

Figure 6:
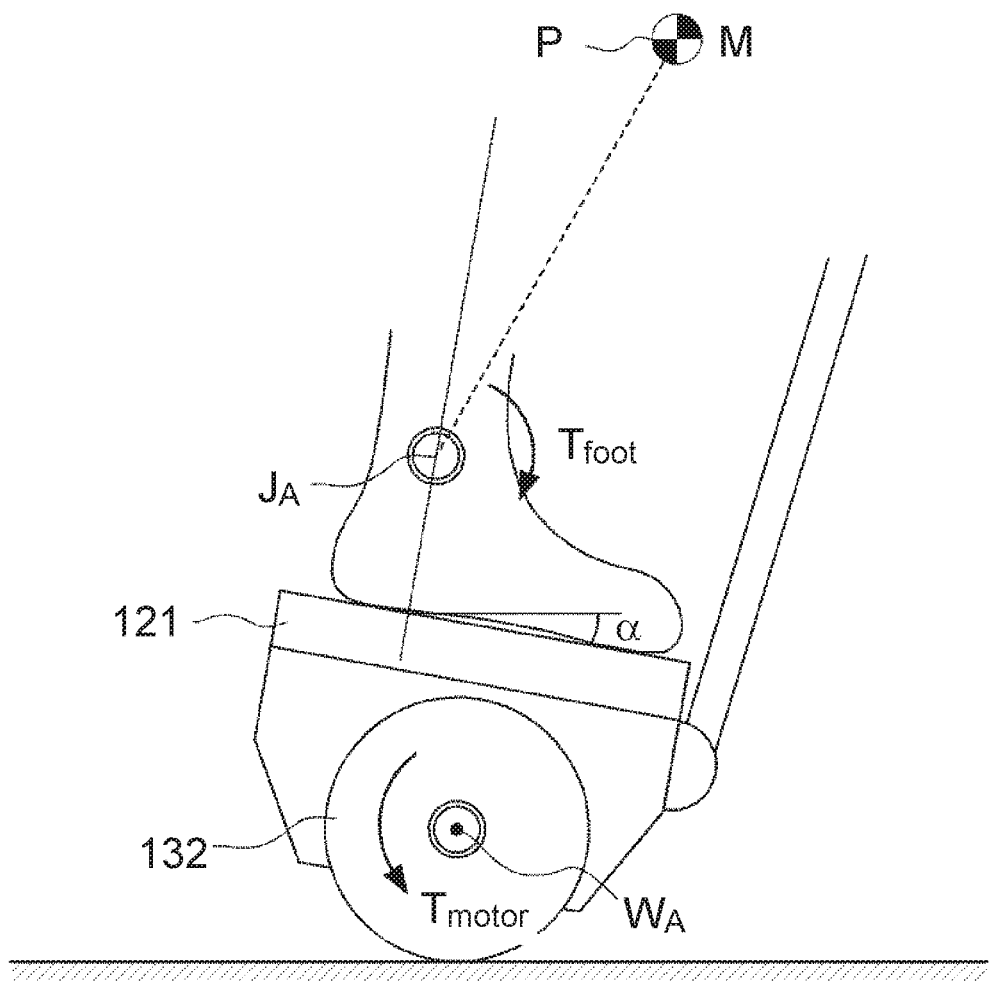
FIG. 6 is a diagram illustrating trial control for training in a passive mode.

Next, the passive mode will be described. FIG. 6 is a diagram illustrating trial control for training in the passive mode. The passive mode is a mode in which the inverted two-wheeled vehicle 100 automatically performs predetermined actions without any instructions intentionally issued by the rider. In the passive mode, a certain degree of training effect can be expected as long as the rider stands on the riding base 121 while keeping the balance. In the passive mode, the controller 200 generates simulative disturbances to make the inverted state unstable, thereby forcing the rider to maintain the balance.

An example of the predetermined actions automatically performed by the inverted two-wheeled vehicle 100 as the simulative disturbances is an action in which the riding base 121 repeats oscillation about the rotation center position $W_A$ of the wheel 132 while the inverted two-wheeled vehicle 100 remains substantially standstill on the spot except for considerably small movements in the front-back direction due to the inverted pendulum control. For example, as illustrated in FIG. 6, the controller 200 tilts the riding surface of the riding base 121 forward by a degrees with respect to the horizontal direction. Then, the rider tries to maintain the balance by adjusting the position of the center of gravity P in the front-back direction and planting the rider's soles firmly on the riding surface, that is, by increasing the ankle-joint torque $T_{foot}$. When the tilt angle α is varied stepwise or continuously, the rider adjusts the magnitude of the ankle-joint torque $T_{foot}$ in accordance with the variations. Such an action of intentionally destabilizing the inverted state to cause the rider to actively maintain the balance is effective as rehabilitation for restoring the ankle-joint function.

It is generally said that the effect of the rehabilitation can be obtained when a patient repeats the action while exerting a force of 40% or higher of a muscle strength that the patient possesses at the time of training. Therefore, a reference value of the ankle-joint torque, at which the effect of the rehabilitation can be obtained, is set for each patient who rides on the inverted two-wheeled vehicle 100, and a maximum value $α_0$ of an oscillation angle is determined such that the patient generates an ankle-joint torque that is higher than the reference value. The rider or an operator inputs the maximum value $α_0$ via the input-operation receiving unit 142 or the input-output IF 144.

The controller 200 oscillates the riding base 121 based on the maximum value $α_0$ that is set as described above. Concurrently with this operation, the controller 200 receives a detection signal from the torque sensor 170, calculates the ankle-joint torque $T_{foot}$, and outputs the ankle-joint torque $T_{foot}$ to, for example, the display unit 140. When the rider succeeds in generating an ankle-joint torque equal to or higher than the reference value more than the predetermined number of times, the controller 200 outputs information indicating the success of the training.

Figure 7:
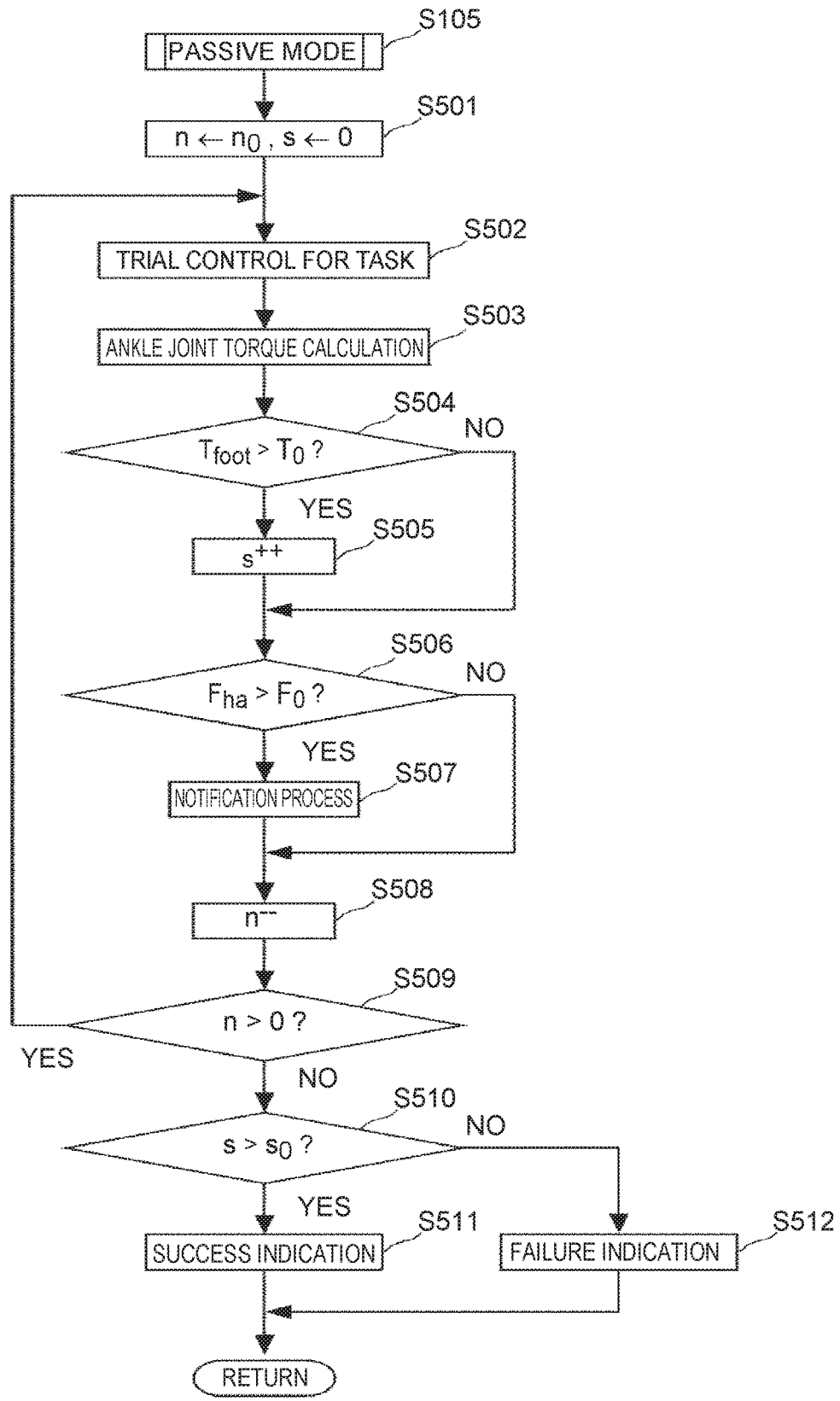
FIG. 7 is a flowchart illustrating a control flow in the passive mode.

FIG. 7 is a flowchart illustrating a control flow in the passive mode (step S105) illustrated as a subfunction in FIG. 5. When the passive mode is started (step S105), in step S501, the controller 200 substitutes an initial value $n_0$ for a repetition count variable n and substitutes zero for a success count variable s.

The controller 200 proceeds to step S502 to start trial control for a training task. Specifically, the controller 200 executes a trial once. In the trial, the riding surface is gradually tilted to the maximum value $α_0$ determined as described above, and then the riding surface is gradually returned to the original horizontal position. Concurrently with this trial, the controller 200 calculates the ankle-joint torque $T_{foot}$ (step S503).

The controller 200 proceeds to step S504 to determine whether the ankle-joint torque $T_{foot}$ exceeds the reference value $T_o$ during the trial executed once in step S502. When the controller 200 determines that the ankle-joint torque $T_{foot}$ has exceeded the reference value $T_o$, the controller 200 increments the success count variable s (step S505) and proceeds to step S506. When the controller 200 determines that the ankle-joint torque $T_{foot}$ has not exceeded the reference value $T_o$, the controller 200 proceeds to step S506 without incrementing the success count variable s.

In step S506, the controller 200 determines whether a component $F_{ha}$ that is included in a force $F_h$ detected by the load sensor 120 and that is perpendicular to a line connecting $W_A$ and $H_P$ to each other exceeds a predetermined threshold load $F_0$ during the trial executed once in step S502. When controller 200 determines that the component $F_{ha}$ has exceeded the threshold load $F_0$, the controller 200 proceeds to step S507 to execute a notification process for notifying that the component $F_{ha}$ has exceeded the threshold load $F_0$, and then proceeds to step S508. When controller 200 determines that the component $F_{ha}$ has not exceeded the threshold load $F_0$, the controller 200 proceeds to step S508 without executing step S507.

The notification process is a process of displaying, for example, a message saying "you lean on the handle too much" on the display unit 140 to notify the rider of the message. In this case, the display unit 140 functions as a notifying unit configured to issue a notification that the threshold load has been exceeded, in cooperation with the controller 200. The notification may be issued by means of not only displaying but also, for example, sound, light, or vibrations. Alternatively, the notification information may be transmitted via the input-output IF 144 to a portable terminal of an assistant who assists the rider in carrying out the training, thereby notifying the assistant of the notification information. In this case, the input-output IF 144 functions as a notifying unit, in cooperation with the controller 200.

If $F_h$ and $F_{ha}$ are not considerably different from each other due to the configuration of the load sensor 120, the controller 200 may directly compare $F_h$ with the threshold load $F_0$. In the process described above, when the threshold load is exceeded during the trial executed once, the controller 200 executes the notification process after the trial. Alternatively, the controller 200 may execute the notification process in substantially real time even during the trial, as, for example, an interrupt process. Conversely, the controller 200 may collectively execute the notification process after determining whether the training succeeds or fails (described later). In this case, the controller 200 may issue a notification about the number of times that the threshold load is exceeded and the times at which the threshold load is exceeded, instead of simply issuing a notification that the threshold load has been exceeded.

In step S508, the controller 200 decrements the repetition count variable n. Then, the controller 200 determines, in step S509, whether the variable n is still larger than zero. When the controller 200 determines that the variable n is still larger than zero, the controller 200 returns to step S502 to repeat the trial control. When the controller 200 determines that the variable n has reached zero, the controller 200 proceeds to step S510.

The controller 200 determines, in step S510, whether the success count variable s has exceeded the reference number of times $s_0$. When the controller 200 determines that the success count variable s has exceeded $s_0$, the controller 200 proceeds to step S511 to display a success indication indicating a success of the training on the display unit 140, based on a determination that the present training will produce an effect. When the controller 200 determines that the success count variable s has not exceeded $s_0$, the controller 200 proceeds to step S512 to display a failure indication indicating a failure of the training on the display unit 140, based on a determination that the present training will not produce an effect. Upon completion of the display, the controller 200 ends the passive mode and returns to the main flow.

In the passive mode described above, the maximum value $\alpha_0$ of the oscillation angle is set in advance, and the controller 200 observes whether the ankle-joint torque $T_{foot}$ exceeds the reference value $T_o$ before the riding surface is tilted to the maximum value $\alpha_0$. However, the riding surface may be controlled to be tilted until the ankle-joint torque $T_{foot}$ exceeds the reference value $T_o$. In this case, the controller 200 functions as a tilt control unit configured to tilt the riding base 121 based on the calculated ankle-joint torque $T_{foot}$, in cooperation with the drive wheel unit 210. When control is executed in this way, the training effect can be obtained reliably.

Figure 8:
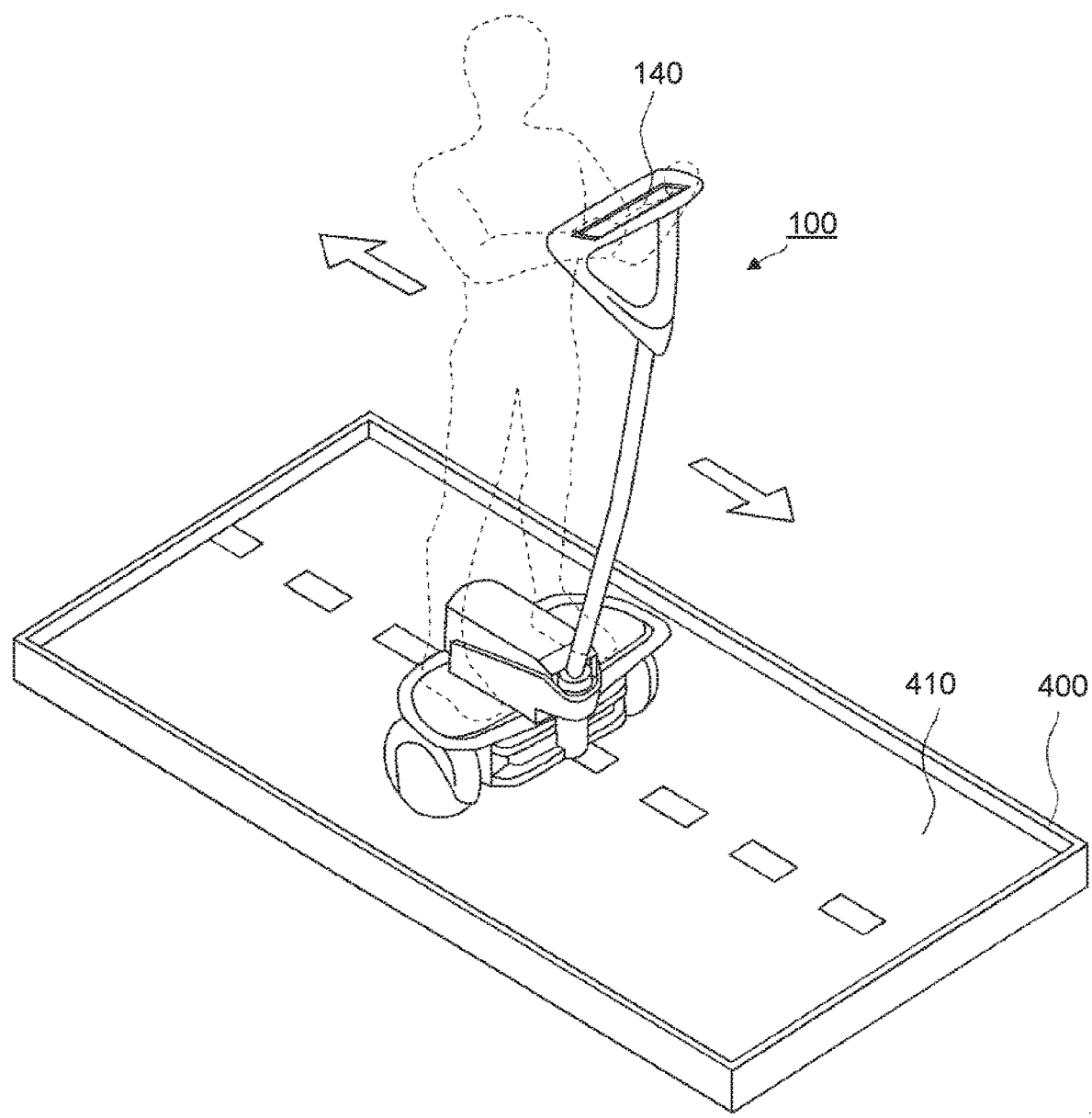
FIG. 8 is a schematic perspective view illustrating how training is carried out in an active mode.

Next, the active mode will be described. FIG. 8 is a schematic perspective view illustrating how training is carried out in the active mode. The active mode is a mode in which a rider moves the inverted two-wheeled vehicle 100 forward and backward while maintaining the balance. In the active mode, the rider carries out training to repeatedly generate an ankle-joint torque higher than a reference value within a predetermined time period.

A training unit 400 includes an enclosed traveling lane 410 (hereinafter, referred to as "traveling lane 410"). The traveling lane 410 has a length of about one meter in the traveling direction, and the rider rides on the inverted two-wheeled vehicle 100 and repeats the back-and-forth travel within the traveling lane 410. The training unit 400 may include, for example, a screen and have an entertainment function of scrolling landscape image forward or backward in accordance with the travel of the inverted two-wheeled vehicle 100.

In a training of a back-and-forth travel within a limited traveling lane as described above, especially when the inverted two-wheeled vehicle 100 shifts from the forward travel to the backward travel or from the backward travel to the forward travel, the rider tries to maintain the balance by planting his/her soles firmly on the riding surface, that is, by increasing the ankle-joint torque $T_{foot}$. This action is effective as rehabilitation for restoring the ankle-joint function. The rider can carry out the training while checking the training progress information displayed on the display unit 140.

As described above, it is generally said that the effect of the rehabilitation can be obtained when a patient repeats the action while exerting a force of 40% or higher of a muscle strength that the patient possesses at the time of training. Therefore, in the active mode as well, a reference value $T_0$ of the ankle-joint torque, at which the effect of the rehabilitation can be obtained, is set for each patient who rides on the inverted two-wheeled vehicle 100. The rider or an operator inputs the reference value $T_0$ via the input-operation receiving unit 142 or the input-output IF 144.

The controller 200 executes traveling control for the back-and-forth travel in response to shifting of the weight of the rider's body. During the traveling control, the controller 200 receives detection signals from the torque sensor 170 and the load sensor 120, calculates the ankle-joint torque $T_{foot}$, and outputs the ankle-joint torque $T_{foot}$ to, for example, the display unit 140. When the rider succeeds in generating an ankle-joint torque, which is equal to or higher than the reference value $T_0$, more than the predetermined number of times within a predetermined time limit, the controller 200 outputs information indicating the success of the training.

Figure 9:
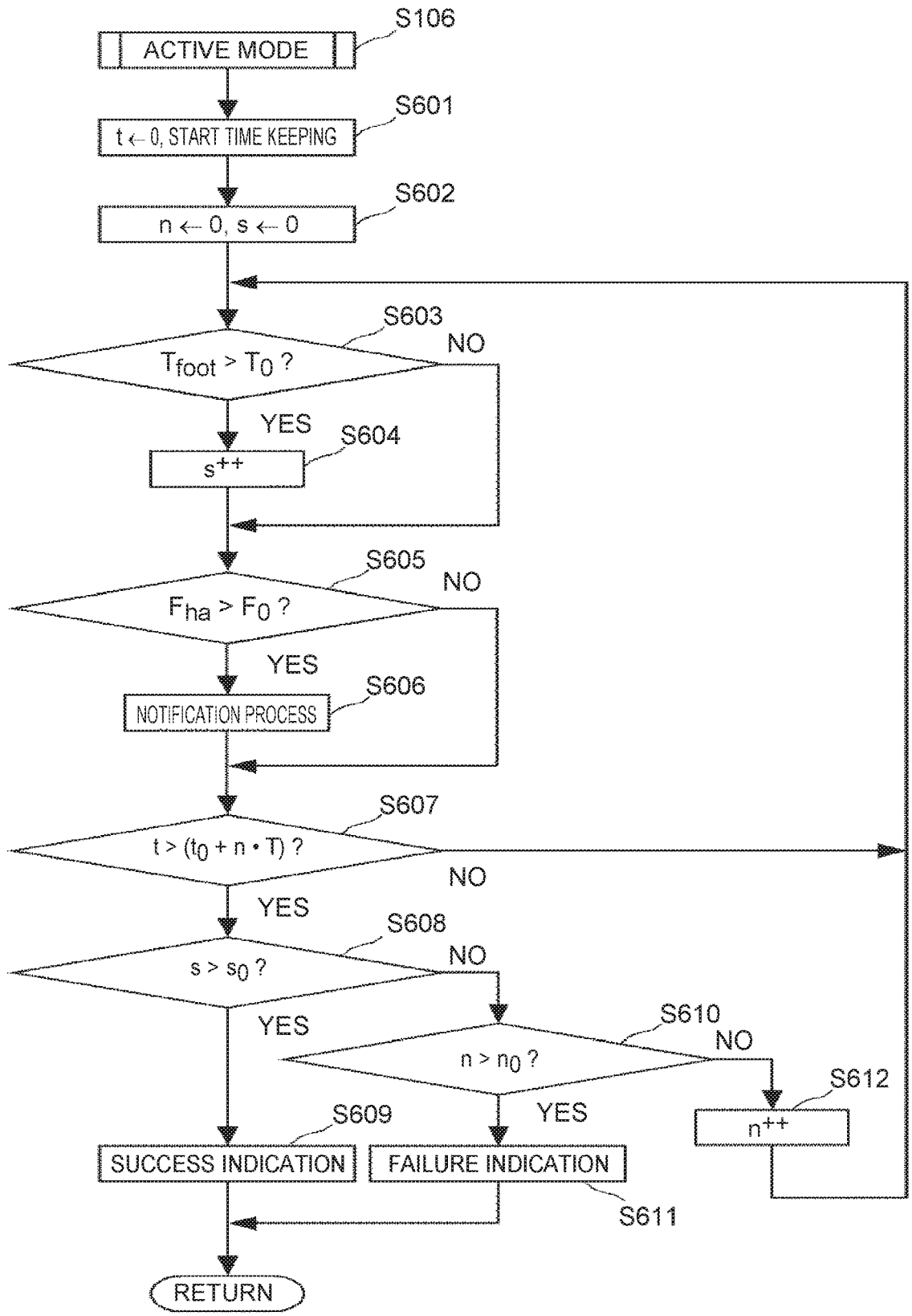
FIG. 9 is a flowchart illustrating a control flow in the active mode.

FIG. 9 is a flowchart illustrating a control flow in the active mode (step S106) illustrated as a subfunction in FIG. 5. When the active mode is started (step S106), the controller 200 clears a timer t and starts time keeping in step S601. In step S602, the controller 200 substitutes zero for an extension count variable n and substitutes zero for a success count variable s. Upon completion of initialization of these variables, the controller 200 starts traveling control in which the inverted two-wheeled vehicle 100 is caused to travel forward and backward in response to shifting of the weight of the rider's body. In addition, the controller 200 starts a process of calculating the ankle-joint torque $T_{foot}$ based on outputs from the torque sensor 170 and the load sensor 120. After checking a message "START" displayed at the start of time keeping, the rider starts the back-and-forth travel of the inverted two-wheeled vehicle 100.

The controller 200 monitors the calculated ankle-joint torque $T_{foot}$ and determines whether $T_{foot}$ has exceeded the reference value $T_0$ (step S603). When the controller 200 determines that $T_{foot}$ has exceeded the reference value $T_0$, the controller 200 increments the success count variable s (step S604) and proceeds to step S605. When the controller 200 determines that $T_{foot}$ has not exceeded the reference value $T_0$, the controller 200 proceeds to step S605 without incrementing the success count variable s.

In step S605, the controller 200 determines whether the component $F_{ha}$ that is included in a force $F_h$ detected by the load sensor 120 and that is perpendicular to a line connecting $W_A$ and $H_P$ to each other has exceeded the predetermined threshold load $F_0$. When the controller 200 determines that the component $F_{ha}$ has exceeded the threshold load $F_0$, the controller 200 proceeds to step S606 to execute a notification process for notifying that the component $F_{ha}$ has exceeded the threshold load $F_0$, and then proceeds to step S607. When the controller 200 determines that the component $F_{ha}$ has not exceeded the threshold load $F_0$, the controller proceeds to step S607 without executing step S606. The details of the notification process are the same as those of the notification process in the passive mode.

The controller 200 determines in step S607 whether the timer t has exceeded a time limit $t_0$. When the extension count variable n is equal to or greater than one, the time limit is set to a time period obtained by adding an extension time period, which is a product of a predetermined unit extension time period T by n, to $t_0$. When the timer t is equal to or shorter than the time limit, the controller 200 returns to step S603. On the other hand, when the timer t has exceeded the time limit, the controller 200 proceeds to step S608.

The controller 200 determines in step S608 whether the success count variable s has exceeded the reference number of times $s_0$. When the controller 200 determines that the success count variable s has exceeded $s_0$, the controller 200 proceeds to step S609 to display a success indication indicating a success of the training on the display unit 140, based on a determination that the present training will produce an effect. When the controller 200 determines that the success count variable s has not exceeded $s_0$, the controller 200 proceeds to step S610.

The controller 200 determines in step S610 whether the extension count variable n has exceeded an upper-limit extension number of times $n_0$ set in advance. When the controller 200 determines that the extension count variable n has not exceeded the upper-limit extension number of times $n_0$, the controller 200 increments the extension count variable n in step S612 and returns to step S603. When the controller 200 determines that the extension count variable n has exceeded the upper-limit extension number of times $n_0$, the controller 200 proceeds to step S611 to display a failure indication indicating a failure of the training on the display unit 140, based on a determination that the present training will not produce an effect. Upon completion of the display in step S609 or step S611, the controller 200 ends the active mode and returns to the main flow.

Figure 10:
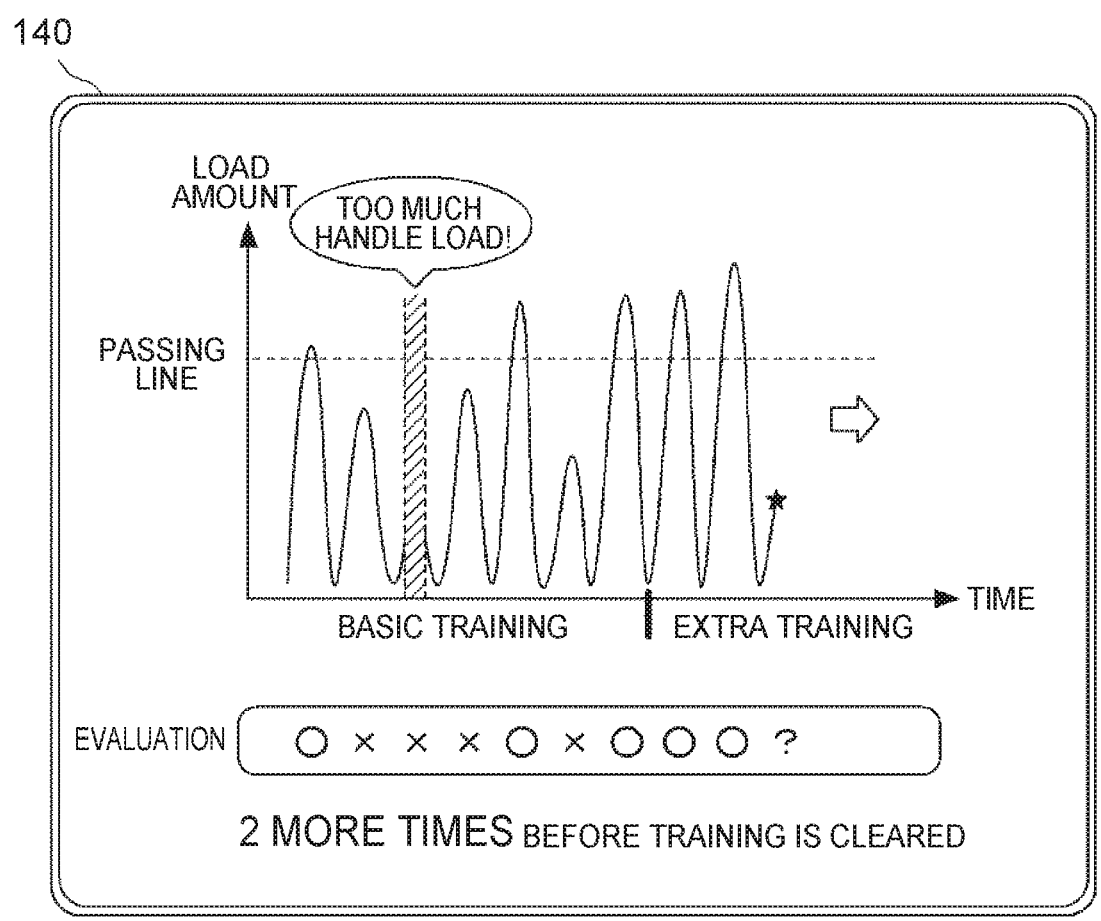
FIG. 10 is a diagram illustrating a display example in the active mode.

FIG. 10 is a diagram illustrating an example of a display on the display unit 140 during execution of the active mode. The graph illustrates the ankle-joint torque $T_{foot}$ as a load amount (ordinate axis), together with the lapse of time (abscissa axis). $T_{foot}$ at the present moment is denoted by an asterisk. The entire waveform is scrolled to the left, and a past portion of the waveform is erased from the left end of the graph. A passing line (acceptable line) denotes the reference value $T_0$. When the load amount indicated by the waveform has exceeded the passing line, a mark "◯" is displayed in an evaluation box. When the load amount indicated by the waveform fails to reach the passing line, a mark "x" is displayed in the evaluation box. Under the abscissa axis indicating the lapse of time, a training executed until the time limit $t_0$ is displayed as "Basic Training", and an extended training is displayed as "Extra Training". Then, the remaining number of times of the training before the reference number of times $s_0$ is reached is displayed.

As illustrated in FIG. 10, when $F_{ha}$ exceeds the threshold load $F_0$ during the training, the controller 200 may erase the asterisk representing $T_{foot}$ at the present moment and gray out a period during which $F_{ha}$ exceeds $F_0$. The controller 200 may additionally execute a notification process by displaying a message, such as "TOO MUCH HANDLE LOAD!". During this period, the controller 200 may stop outputting the torque information or may output the torque information together with additional information, such as a flag indicating that $F_{ha}$ has exceeded the threshold load $F_0$. When the torque information is recorded as an item of a continuous log, the controller 200 may record the torque information together with the additional information.

Not only the display information as illustrated in FIG. 10 but also various kinds of other information may be displayed. For example, load amounts may be accumulated and displayed in the form of a gauge, or a message, such as "You should plant your feet more firmly". Such a display allows the rider to check the training progress status. Such a display also contributes to an increase in the rider's training motivation.

Figure 11:
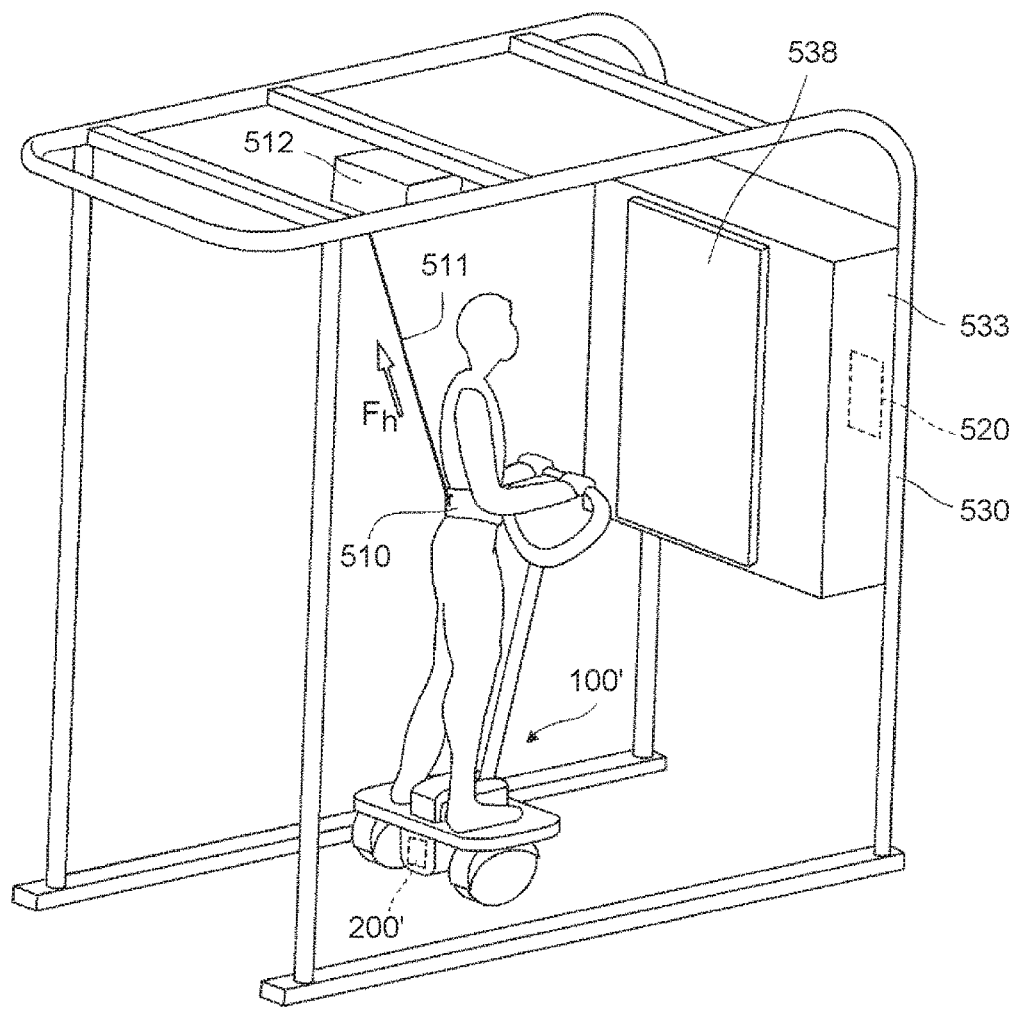
FIG. 11 is a perspective view of the appearance of a training apparatus according to another embodiment.

In the foregoing embodiment, the inverted two-wheeled vehicle 100 constitutes the entire training system. Alternatively, the inverted two-wheeled vehicle 100 may constitute a part of the training system. FIG. 11 is a perspective view of the appearance of a training apparatus 500 according to another embodiment.

The training apparatus 500 is a training system that includes an inverted two-wheeled vehicle 100' having substantially the same configuration as that of the inverted two-wheeled vehicle 100 described above. The training apparatus 500 mainly includes a harness pulling unit 512 attached to a frame 530 that constitutes an overall framework, in addition to the inverted two-wheeled vehicle 100'. A rider causes the inverted two-wheeled vehicle 100' to travel on a traveling lane surrounded by the frame 530, thereby carrying out a training.

The frame 530 supports, for example, a control board 533 that houses an overall control unit 520 configured to control a motor and a sensor, and a display unit 538 that is, for example, a liquid crystal panel for displaying a training progress status and so forth. In addition, the frame 530 supports the harness pulling unit 512 in the vicinity of an area over the rider's head. The overall control unit 520 is, for example, a central processing unit (CPU). The overall control unit 520 communicates with a controller 200' included in the inverted two-wheeled vehicle 100' to collectively control the entirety of the training apparatus 500.

The training apparatus 500 includes a safety device including a harness 510, a harness wire 511, and the harness pulling unit 512, as main components. The harness 510 is a belt to be wound around the rider's waist, and to be secured to the rider's waist through, for example, a hook-and-loop fastener. The harness 510 is coupled to one end of the harness wire 511, which is a hanging tool.

The other end of the harness wire 511 is coupled to a winding-up mechanism of the harness pulling unit 512. The winding-up mechanism of the harness pulling unit 512 is configured to wind up or unwind the harness wire 511 as a motor (not illustrated) is turned on or off. The harness pulling unit 512 including the motor (not illustrated) functions as a driving unit configured to pull up or down the harness wire 511. With this configuration, when the rider is about to lose the balance, the safety device supports the upper body of the rider to stabilize the rider.

In this device configuration, the harness wire 511 to be fitted to the rider's waist serves as an assisting support portion configured to assist the rider in maintaining the balance. At this time, a load cell included in the harness pulling unit 512 detects a pulling force $F_h$ with which the rider pulls the harness wire 511 when the rider nearly is about to lose the balance. When the pulling force $F_h$ is detected, it is possible to calculate the ankle-joint torque $T_{foot}$ with the influence of the pulling force $F_h$ eliminated, as described above with reference to FIG. 4. That is, even when the rider applies a load to a portion other than the handle in order to maintain the balance, it is possible to calculate the ankle-joint torque $T_{foot}$ with the influence of the load eliminated.

While the modified example has been described above, an object to which a rider applies a load to maintain the balance is not limited to the handle or the harness wire, and various kinds of components may be an object to which a rider applies a load to maintain the balance. For example, in the case of an inverted two-wheeled vehicle without a handle, the inverted two-wheeled vehicle may include a component, such as a supporting rod fixed to a base, and a rider holds the supporting rod with his/her inner thighs in order to maintain the balance.

What is claimed is:

1. A training system for carrying out a rehabilitation training by a rider, comprising:
    an inverted-pendulum mobile body including a drive wheel and a riding portion on which a rider rides trying to keep riding, while maintaining a balance, in a standing position;
    a first detector configured to detect a driving torque that is applied to the drive wheel to maintain the inverted-pendulum mobile body in an inverted state;
    a second detector configured to detect a load applied by the rider to an assisting support portion configured to assist the rider in maintaining the balance;
    an acquiring unit configured to acquire specific information regarding the rider, the specific information including a body weight and a foot size of the rider;
    a controller configured to generate torque information about an ankle-joint torque applied by the rider to the riding portion, based on the driving torque detected by the first detector, the load detected by the second detector, and the body weight and the foot size of the rider, and configured to output the torque information; and
    a notifying unit configured such that, when the load detected by the second detector has exceeded a threshold load set in advance, the notifying unit notifies the rider that the load has exceeded the threshold load.

2. The training system according to claim 1, wherein the notifying unit is configured to notify the rider of the fact that the load has exceeded the threshold load by sound.

3. The training system according to claim 1, wherein, when the load detected by the second detector has exceeded a threshold load set in advance, the controller outputs the torque information after adding additional information to the torque information.

4. The training system according to claim 1, wherein the assisting support portion includes a handle provided in the inverted-pendulum mobile body and configured to be held by the rider.

5. The training system according to claim 1, wherein the assisting support portion includes a hanging tool provided independently of the inverted-pendulum mobile body and fitted to an upper body of the rider.

6. The training system according to claim 1, further comprising a switch configured to execute switching between an active mode and a passive mode, each set as a training mode in which an ankle joint of the rider is trained, the active mode being a mode in which the inverted-pendulum mobile body travels in response to shifting of the rider's center of gravity, and the passive mode being a mode in which a simulative disturbance is generated to make the inverted state unstable.

7. The training system according to claim 1, wherein the controller is further configured to tilt the riding portion based on the torque information.

8. The training system according to claim 1, wherein the controller is configured to generate the torque information based on the driving torque at a time when the inverted-pendulum mobile body is not making a turn.

9. The training system according to claim 1, wherein the controller is further configured to count the number of times the ankle-joint torque is estimated to exceed a threshold value set in advance, based on the torque information, and configured to present the number of times the ankle-joint torque is estimated to exceed the threshold value.

10. An ankle-joint torque estimating method for estimating an ankle-joint torque of a rider, comprising:
    detecting a driving torque that is applied to a drive wheel of an inverted-pendulum mobile body to maintain the inverted-pendulum mobile body in an inverted state, the inverted-pendulum mobile body including the drive wheel and a riding portion on which the rider rides in a standing position;
    detecting a load applied by the rider to an assisting support portion configured to assist the rider in maintaining a balance;
    acquiring specific information regarding the rider, the specific information including a body weight and a foot size of the rider;
    generating an estimated value of the ankle-joint torque of the rider based on the driving torque, the load, the body weight, and the foot size; and
    when the detected load has exceeded a threshold load set in advance, notifying the rider that the load has exceeded the threshold load.

* * * * *